United States Patent
Nokita

(10) Patent No.: US 6,839,401 B2
(45) Date of Patent: Jan. 4, 2005

(54) X-RAY COMPUTED TOMOGRAPHY APPARATUS

(75) Inventor: Makoto Nokita, Tochigi (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 10/716,738

(22) Filed: Nov. 17, 2003

(65) Prior Publication Data

US 2004/0161073 A1 Aug. 19, 2004

(30) Foreign Application Priority Data

Nov. 19, 2002 (JP) .................................. 2002-335637

(51) Int. Cl.⁷ .................. G01N 23/201; A61B 6/00
(52) U.S. Cl. ............................................. 378/7; 378/98.4
(58) Field of Search ................. 378/4–20, 98.4

(56) References Cited

U.S. PATENT DOCUMENTS

| | | |
|---|---|---|
| 4,807,267 A | 2/1989 | Rifu et al. |
| 5,615,279 A | 3/1997 | Yoshioka et al. |
| 6,744,845 B2 * | 6/2004 | Harding et al. ............... 378/16 |

FOREIGN PATENT DOCUMENTS

| | | |
|---|---|---|
| EP | 0 660 421 A2 | 6/1995 |
| JP | 62-261342 | 11/1987 |
| JP | H07-124150 | 5/1995 |
| JP | H07-63464 B | 7/1995 |
| JP | H08-116044 | 5/1996 |
| JP | H09-255046 | 6/1999 |

* cited by examiner

Primary Examiner—Craig E. Church
Assistant Examiner—Krystyna Suchecki
(74) Attorney, Agent, or Firm—Morgan & Finnegan, LLP

(57) ABSTRACT

In order to remove a scattered line component resulting from an object from projection data to obtain a satisfactory rearrangement image, an amount of scattered line is calculated from a region in which a first-order X-ray is shielded by an X-ray shield and a component corresponding to the scattered line is removed. Then, an image in the region in which the first-order X-ray is shielded is complemented based on an image taken from a 180-degree opposite direction.

6 Claims, 8 Drawing Sheets

X-RAY COMPUTED TOMOGRAPHY APPARATUS

BACKGROUND OF THE INVENTION

1. Field of the Invention

The present invention relates to an X-ray computed tomography apparatus having an X-ray shield, and more particularly to a removal of a scattered line by detecting an amount of the scattered line from a region in which a first-order X-ray is shielded by the X-ray shield in a state in which the X-ray shield is located between a focal point of an X-ray source and an X-ray detection device.

2. Related Background Art

In recent years, an X-ray sensor capable of directly converting an X-ray image into a digital output in real time has been proposed. For example, it is possible to manufacture a solid light detection device in which solid light detection elements, each of which is composed of a transparent conductive film and a conductive film, are arranged in two-dimensional matrix on a substrate made of quartz glass with an amorphous semiconductor film interposed therebetween. Thus, the X-ray sensor is an X-ray detection device in which the solid light detection device and a scintillator that converts X-rays into visible lights are laminated.

Regarding a process that obtains an X-ray digital image in the case where the X-ray detection device is used, when the X-ray detection device is irradiated with the X-rays that pass through an object, the X-rays are converted into the visible lights by the scintillator and the converted visible lights are detected as electrical signals by photoelectric conversion portions of the solid light detection elements.

The electrical signals are read from the respective solid light detection elements by a predetermined reading method. An A/D conversion is performed on the read electrical signals to obtain X-ray image signals. The detection device is described in detail in Japanese Patent Application Laid-Open No. H08-116044.

Also, a large number of detection devices that directly obtain X-rays by the solid light detection device without using the scintillator have been proposed. Those detection devices have no light scattering resulting from the scintillator as compared with the case of the detection device using the scintillator. Accordingly, it is generally said that the resolution is preferable.

Further, a large number of detection devices in which a CCD or a CMOS detection device is combined with the scintillator to increase the number of times image taking is performed per unit time have been proposed. Hereinafter, such an X-ray sensor capable of directly converting an X-ray image into a digital output in real time is called an X-ray detection device.

An X-ray computed tomography apparatus using the X-ray detection device has been proposed.

In a conventional X-ray computed tomography apparatus, a one-dimensional X-ray detection device in which detection elements are arranged in one-dimensional line is used to rearrange only a cross-section of an object, thereby obtaining a slice image of the object. In the case where a two-dimensional X-ray detection device in which detection elements are arranged in two-dimensional matrix is used, not only the slice image of the object but also a three-dimensional image thereof can be obtained.

In the case where the one-dimensional X-ray detection device is used, X-rays radiated from an X-ray source are collimated so as to form a fan beam according to a width of the one-dimensional X-ray detection device. In contrast to this, in the case where the two-dimensional X-ray detection device is used, X-rays radiated from the X-ray source may be collimated according to a size of the two-dimensional X-ray detection-device. Accordingly, it is generally said that the X-rays form a cone beam.

Hereinafter, an X-ray computed tomography apparatus which uses the fan beam X-rays and includes the one-dimensional X-ray detection device is called a fan beam CT. In addition, an X-ray computed tomography apparatus which uses the cone beam X-rays and includes the two-dimensional X-ray detection device is called a cone beam CT.

Regarding the fan beam CT, in the case where a three-dimensional image of an object is obtained, it is necessary that scanning of the object and its vicinities is conducted plural times to obtain a plurality of slice images and the obtained slice images are combined with one another. Therefore, a large amount of heat is generated in the X-ray source to apply a large amount of load to the X-ray source. In addition, an image taking time required for obtaining the three-dimensional image is lengthened, so that the burden is put upon a patient as the object.

Regarding the cone beam CT; although depending on the size of the two-dimensional X-ray detection device, the three-dimensional image of the object can be obtained by conducting scanning on the object and its vicinities only once. Accordingly, the image taking time can be shortened and the load to the X-ray source can be reduced.

Note that a part of X-rays entered onto the object is scattered. Therefore, in addition to first-order X-rays directly entered from the X-ray source onto the X-ray detection device through the object, the scattered X-rays also enter onto the X-ray detection device and are thus detected.

The amount of scattered X-ray is about 20% of the total detection amount in the case of the fan beam CT. In contrast to this, in the case of the cone beam CT, the amount of scattered X-ray is equal to or larger than half of the total detection amount. Therefore, there is a problem in that the accurate image rearrangement is impossible.

SUMMARY OF THE INVENTION

Therefore, an object of the present invention is to provide an X-ray computed tomography apparatus in which an X-ray shield is located between a focal point of an X-ray source and an X-ray detection device on a traveling path of X-rays which are entered from the focal point of the X-ray source onto the X-ray detection device through an object, an amount of scattered line is detected from an X-ray detection device region in which first-order X-rays are shielded by the X-ray shield, and the scattered lines are removed by the acquired data, so that a preferable image which is not influenced by the scattered lines can be obtained.

According to the present invention, the foregoing object is attained by providing an X-ray computed tomography apparatus, including:

an X-ray source that radiates an X-ray to an object;

an X-ray detection device that converts the X-ray passing through the object into image data;

at least one X-ray shield located between a focal point of the X-ray source and the X-ray detection device;

control means for performing control so as to relatively move the X-ray source and the object;

scattered line removing means for calculating an image component corresponding to a scattered line from image data corresponding to a region in which a first-order X-ray is shielded by the X-ray shield and calculating a process image obtained by removing the image component from the image data;

complementing means for calculating from the process image a complement image data obtained by complementing the image data corresponding to the region in which the first-order X-ray is shielded; and rearranging means for rearranging an image by reversely projecting the complement image data, in which the complementing means complements the process image based on image data converted from an X-ray radiated along an X-ray path in a 180-degree opposite direction to an X-ray path connecting the focal point of the X-ray source with the X-ray shield.

Other objects, features and advantages of the present invention will be apparent from the following descriptions taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate an embodiment of the invention and, together with the descriptions, serve to explain the principle of the invention.

DESCRIPTION OF THE PREFERRED EMBODIMENTS

A preferred embodiment of the present invention will be described in detail in accordance with the accompanying drawings.

The following is an embodiment of an X-ray computed tomography apparatus in which scattered lines resulting from an object are removed to conduct a suitable image rearrangement.

Figure 1:
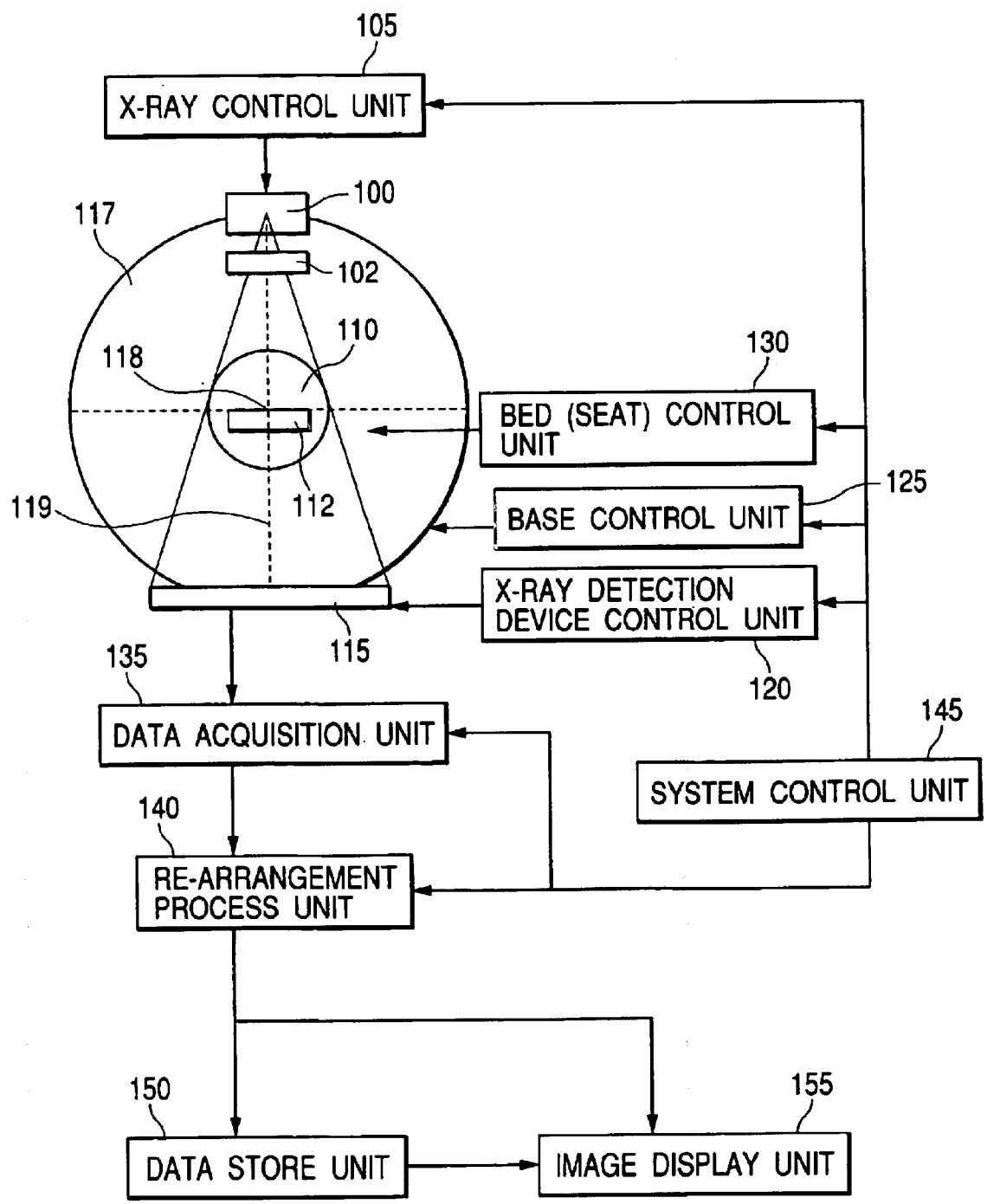
FIG. 1 is a schematic structural diagram showing a preferred example of an X-ray computed tomography apparatus of the present invention.

FIG. 1 is a schematic structural diagram showing a preferred example of an X-ray computed tomography apparatus according to this embodiment. In FIG. 1, reference numeral 100 denotes an X-ray source for projecting X-ray onto the object, 102 denotes an X-ray aperture for restricting projection area of X-ray, 105 denotes an X-ray control unit, 110 denotes an image taking region in which it is possible to rearrange an image, 112 denotes a bed (seat) for supporting the object, 115 denotes an X-ray detection device, 117 denotes a base for supporting the X-ray source 100 and the X-ray detection device 115, 118 denotes a rotation axis of rotational movement of the base 117, 119 denotes a central line perpendicularly connecting a focus point of the X-ray source 100 with the rotation axis 118, 120 denotes an X-ray detection device control unit, 125 denotes a base control unit, 130 denotes a bed (seat) control unit, 135 denotes a projection data acquisition unit, 140 denotes a rearrangement process unit, 145 denotes a system control unit, 150 denotes a data store unit, and 155 denotes an image display unit.

First, an irradiation area of an X-ray radiated from the X-ray source 100 held to the base 117 is reduced to the size of the X-ray detection device 115 by the X-ray aperture 102. Then, the reduced X-ray passes through an object, which is supported on the bed (seat) 112 and located within an image taking region 110, and enters onto the X-ray detection device 115 held to the base 117.

The incident X-ray is obtained as projection data by the X-ray detection device 115. The above-mentioned process is conducted for scanning the object and its vicinities while the base 117 is rotated about the rotation axis 118, thereby obtaining projection data in all directions. In addition to this, the bed (seat) 112 that supports the object can be moved to helically scan the object and its vicinities, thereby obtaining the projection data.

The system control unit 145 synchronizes the X-ray control unit 105, the X-ray detection device control unit 120, and the base control unit 125 so as to be able to detect an X-ray radiated at each projection angle by the X-ray detection device 115.

The X-ray control unit 105 controls an X-ray irradiation from the X-ray source 100. The X-ray detection device control unit 120 controls signal accumulation, signal transfer, signal discharge, and the like on each pixel in the X-ray detection device 115. The base control unit 125 controls the rotation operation of the base 117. In the case of helical scanning, in addition to these controls, the bed (seat) control unit 130 controls the bed (seat) 112.

The acquired projection data is stored in the projection data acquisition unit 135. The projection data at each angle is stored with relation to image taking information such as an image taking angle, which is received from the system control unit 145.

Regarding the stored projection data at each angle, after obtaining X-ray detection image on which preprocess for correcting variation on each pixels is performed, a scattered X-ray component resulting from the object is removed from a detection component of the X-ray detection device 115 which is the X-ray detection image, by the rearrangement process unit 140. Accordingly, the projection data is corrected to first-order X-ray image including only a first-order X-ray component and stored in the rearrangement process unit 140 or the projection data acquisition unit 135. Then, image rearrangement is conducted using the first-order X-ray image at each angle. The rearranged image data is stored in the data store unit 150 and displayed as an image on the image display unit 155 to observe the image for diagnosis.

Figure 2A:
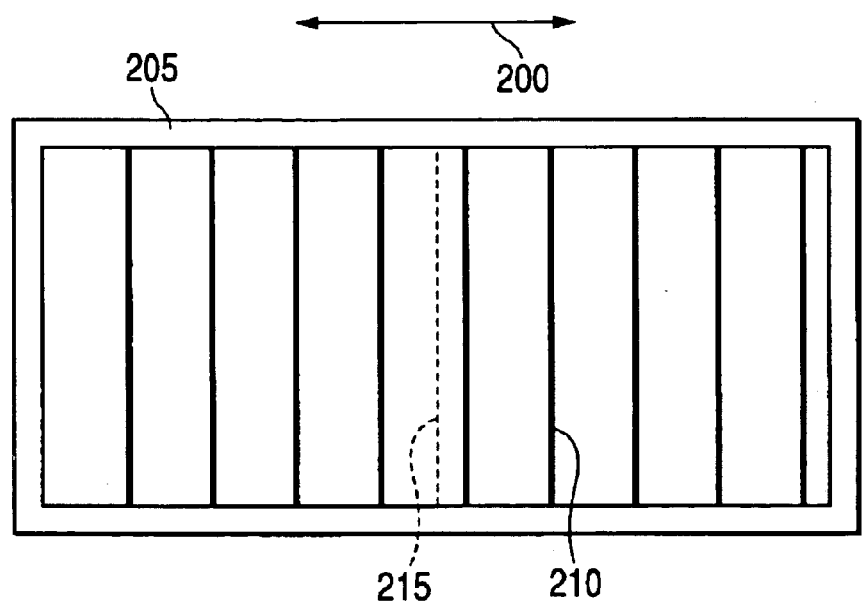
FIGS. 2A and 2B are explanatory views of first-order X-ray shields for scattered line component extraction.
Figure 2B:
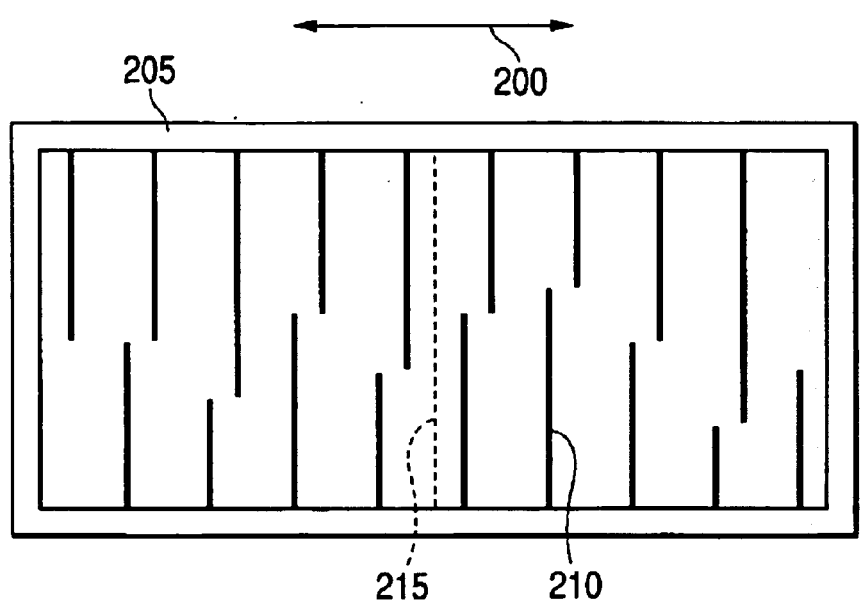

FIGS. 2A and 2B are explanatory views of first-order X-ray shields for scattered line component extraction. Reference numeral 200 denotes a rotational direction of the base. The rotational direction of the base is generally called a slice direction. An X-ray aperture 205 is formed such that an irradiation area of an X-ray from the X-ray source 100 is reduced to almost the same size as the detection surface of the X-ray detection device 115, to prevent redundant X-ray irradiation to the object.

Also, in the case where the X-ray irradiation area to the object is reduced, the amount of scattered line is reduced and there is an effect to improve an image quality. X-ray shields 210 are fixed to the X-ray aperture 205.

The first-order X-ray, which directly entered from the X-ray source 100 onto the X-ray detection device 115 through the object, is blocked by the X-ray shields 210. Only the scattered line resulting from the object is entered onto a region of the X-ray detection device 115, which is shield from the first-order X-ray, so that the detection amount in the region which is shield from the first-order X-ray is assumed to be the amount of the scattered line.

A symmetrical line 215 is a line produced by cutting the X-ray aperture 205 by a plane which includes the X-ray focal point of the X-ray source 100 and the rotational axis of the base 117. Here, the feature is that the X-ray shields 210 are asymmetrically arranged with respect to the symmetrical line 215. Regarding the asymmetrical arrangement of the X-ray shields 210, there is an advantage that it is unnecessary to arrange the X-ray shields 210 with high precision and the X-ray shields 210 can be produced at low cost.

The X-ray shields 210 can be located between the object and the X-ray detection device 115 on a path from the X-ray source 100 to the X-ray detection device 115 through the object. In the case where the X-ray shields 210 are located between the X-ray source 100 and the object, the object is not irradiated with the X-ray at an X-ray shield region. Therefore, an effect is provided in that the dose of the object is reduced.

A further effect resulting from the asymmetrical arrangement of the X-ray shields 210 will be described with reference to FIGS. 4 and 5. A difference between FIGS. 2A and 2B shows that an arrangement manner of the X-ray shields 210 is arbitrary other than the asymmetry with respect to the symmetrical line.

Figure 3:
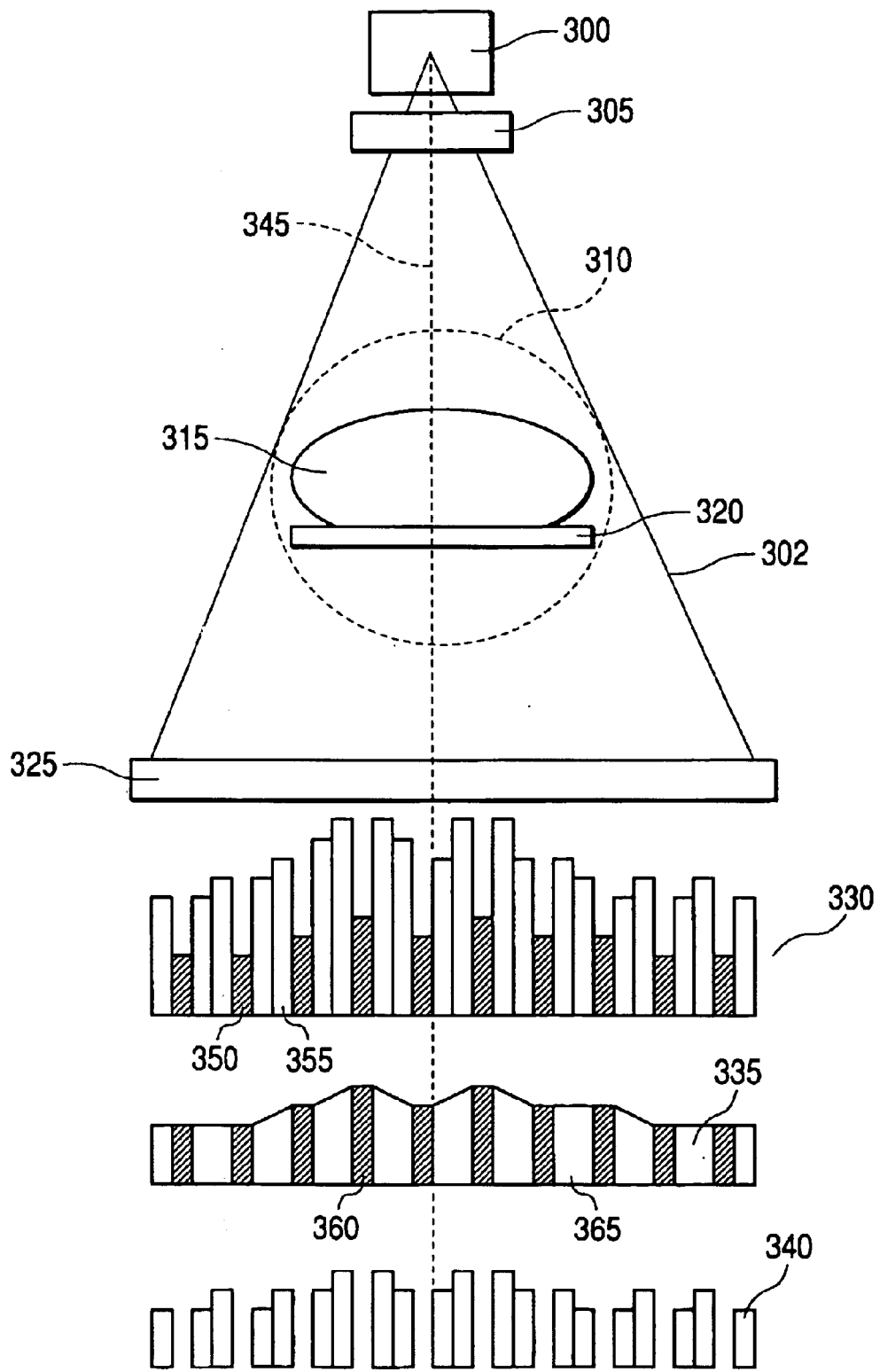
FIG. 3 is an explanatory view of a process for removing a scattered line component from a detection value of an X-ray detection device.

FIG. 3 is an explanatory view of a process for removing a scattered line component from a detection value of the X-ray detection device 115. Reference numeral 300 denotes an X-ray source, 302 denotes an X-ray, 305 denotes an X-ray aperture, 310 denotes an image taking region, 315 denotes an object, 320 denotes a bed, 325 denotes an X-ray detection device, 330 denotes X-ray detection image data corresponding to an X-ray detection component, 335 denotes a scattered X-ray data corresponding to a scattered X-ray component, 340 denotes a first-order X-ray data corresponding to a first-order X-ray component, and 345 denotes a central line which is the same as the central line 19. In this arrangement, the X-ray detection image data 330 is the X-ray detection image described in the explanation of FIG. 1. In addition, reference numeral 350 denotes a first-order X-ray shield region, 355 denotes a first-order X-ray non-shield region, 360 denotes a scattered X-ray detection part, and 365 denotes a scattered X-ray complemented part.

The X-ray 302 is radiated from the X-ray source 300 and passes through the object 315 supported on the bed 320 located within the image taking region 310. Then, the X-ray 302 enters onto the X-ray detection device 325 and is thus detected. An X-ray irradiation region is reduced to a detectable region of the X-ray detection device 325 by the X-ray aperture 305. When the X-ray source 300 and the X-ray detection device 325 are rotated to conduct scanning at each direction, X-ray detection image data 330 at each direction which is used for rearranging an image within the image taking region 310 is obtained.

In the case where one X-ray detection image data of image data 330 is checked, in a region where a line that connects the focal point of the X-ray source 300 with the X-ray shields 210 shown in FIGS. 2A and 2B intersects the X-ray detection device 325, the first-order X-ray is shielded, so that only the scattered line from the object is detected in the region. On the other hand, both the first-order X-ray and the scattered line are detected in the other region.

This is indicated by the X-ray detection image 330. Black portions of the X-ray detection image 330 correspond to first-order X-ray shield regions 350 (only the scattered line) and white portions thereof correspond to first-order X-ray non-shield regions 355 (sum of the first-order X-ray and the scattered line). In the case where the scattered X-ray data 335 is extracted from the X-ray detection image 330, there is an example in which components in the black first-order X-ray shield regions 350 (only the scattered line) are extracted without processing and components in the other regions are interpolated using components in the black first-order X-ray shield regions 350 (only the scattered line).

In this example, linear interpolation using the two black first-order X-ray shield regions (only the scattered line) located at both sides or the two adjacent black first-order X-ray shield regions on one side is conducted on the scattered X-ray data 335. Weighting depends on an interpolation position. The reason why such interpolation can be conducted on the scattered X-ray data 335 is because the scattered line component 335 from the arbitrary object 315 has only a very slow frequency component.

The scattered X-ray data 335 is subtracted from the X-ray detection image 330 to obtain the first-order X-ray data 340. Components corresponding to positions of the first-order X-ray shield regions (only the scattered line) are not present in the first-order X-ray data 340. Therefore, the example in which linear interpolation using the two white first-order X-ray regions located at both sides or the two adjacent white first-order X-ray shield regions on one side is conducted on the first-order X-ray data 340. Weighting depends on an interpolation position.

High frequency components of the first-order X-ray data 340 are larger than high frequency components of the scattered line data 335. Therefore, it is important to make the size of the first-order X-ray shield regions smaller than the size of the first-order X-ray non-shield regions.

The central line 345 is identical to the symmetrical line 215 shown in FIGS. 2A and 2B. As shown in FIGS. 2A, 2B and 3, the X-ray shields 210 are located between the X-ray source 300 and the X-ray detection device 325. Accordingly, an effect is provided in that the scattered X-ray data 335 resulting from the object, by which a quality of a rearrangement image is deteriorated can be removed from the X-ray detection image 330 to obtain a satisfactory rearrangement image.

Figure 4:
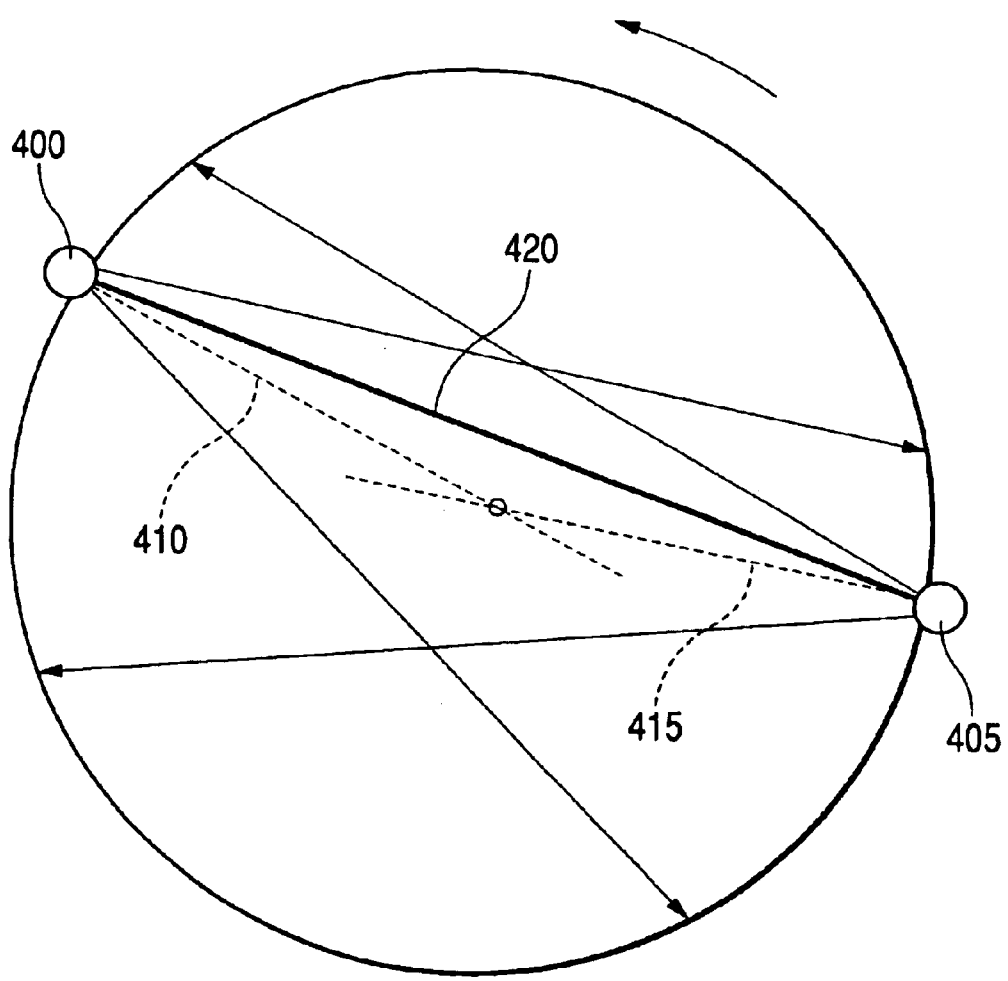
FIG. 4 is an explanatory view of interpolation of a first-order X-ray data 340 in a first-order X-ray shield region.

FIG. 4 is an explanatory view of interpolation of the first-order X-ray data 340 in the first-order X-ray shield region. Reference numerals 400 and 405 denote X-ray sources, 410 and 415 denote central lines, and 420 denotes 180-degree opposite X-ray paths.

The X-ray source 400 is moved to a position of the X-ray source 405 by the rotation of the base. The rotational center at this time is an intersection between the central line 410 and the central line 415. A direction of an X-ray radiated from the X-ray source 400 corresponds to a direction of an X-ray radiated from the X-ray source 405. These are indicated by the 180-degree opposite X-ray paths 420.

As is apparent from FIG. 4, the respective 180-degree opposite X-ray paths 420 are symmetrical with respect to the central lines 410 and 415 in the case where the respective 180-degree opposite X-ray paths 420 are viewed from the X-ray sources 400 and 405. Therefore, when the X-ray source 400 is rotated one revolution for scanning by the rotation of the base, the number of X-ray paths in a direction, which passes through an arbitrary point within the image taking region 310 is necessarily two. The two X-ray paths become the 180-degree opposite X-ray paths 420 and they have a symmetrical relationship with respect to the central line 410 that passes through the X-ray source 400 and the rotational center.

Therefore, if the X-ray shields 210 are asymmetrically arranged with respect to the symmetrical line 215 as shown in FIGS. 2A and 2B, the X-ray detection image 330 in the first-order X-ray shield regions can be interpolated using the 180-degree opposite X-ray paths 420.

In general, the scattered X-ray data 335 resulting from the object 315 includes only low frequency components but the first-order X-ray data 340 includes a large number of high frequency components. Accordingly, in the case where components in the first-order X-ray shield regions are interpolated using the surrounding first-order X-ray components, there is a fear that missing image information is caused.

Also, in order for the scattered line to be accurately measured from the first-order X-ray shield regions, some size is required. Therefore, a contrary effect is produced between a reduction in missing image information and an accurate extraction of the scattered X-ray data 335.

Thus, in the case where the X-ray detection image 330 in the first-order X-ray shield regions is interpolated using the 180-degree opposite X-ray paths 420, an effect is provided in that the reduction in missing image information and the accurate extraction of the scattered X-ray data 335 are compatible to obtain a satisfactory rearrangement image.

Figure 5:
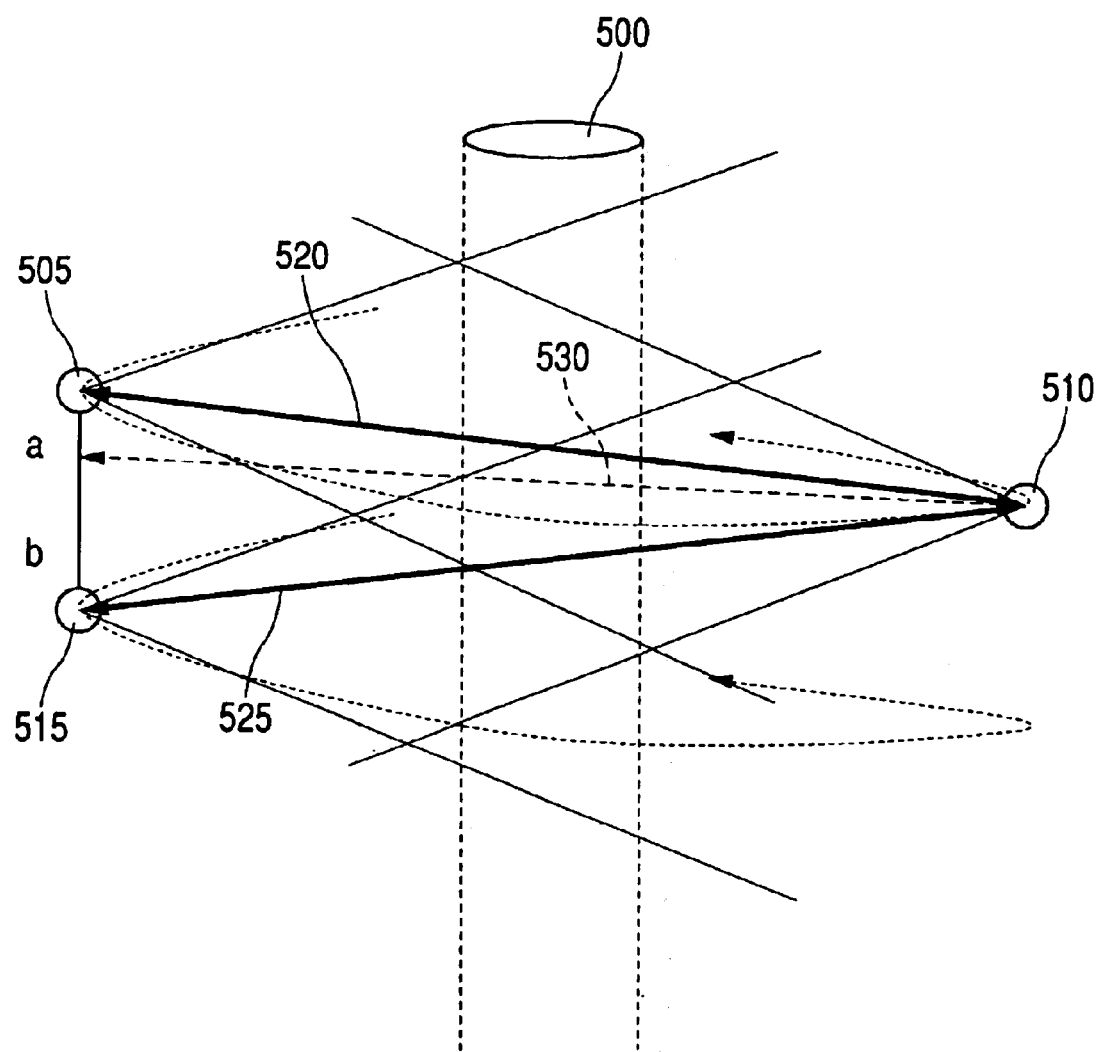
FIG. 5 is an explanatory view of interpolation of a first-order X-ray data 340 in the first-order X-ray shield region in the case of helical scanning.

FIG. 5 is an explanatory view of interpolation of the first-order X-ray data 340 in the first-order X-ray shield region in the case of helical scanning. Reference numeral 500 denotes an image taking region, 505 denotes an X-ray source (N_0), 510 denotes an X-ray source (N_180), 515 denotes an X-ray source (N+1_0), 520 denotes a 180-degree opposite X-ray path, 525 denotes a 180-degree opposite X-ray path 420, and 530 denotes an interpolation X-ray path.

A manner in which the bed 112 is moved while the X-ray source 100 and the X-ray detection device 115 are rotated in the base 117 shown in FIG. 1 corresponds to that in which the image taking region 500 is helically scanned. The X-ray source (N_0) 505 reaches a position of the X-ray source (N_180) 510, and then, reaches a position of the X-ray source (N+1_0) 515. Here, N in ( ) indicates an nth revolution. In addition, 0 and 180 in ( ) indicate that, in the case where FIG. 5 is viewed from a direction of the image taking region 500, a relationship between a combination of the X-ray source (N_0) 505 and the X-ray source (N+1_0) 515 and the X-ray source (N_180) 510 becomes a relationship between the X-ray source 400 and the X-ray source 405 as shown in FIG. 4.

In the case where both the X-ray source 100 and the X-ray detection device 115 are extended in the rotational axis direction, there are the 180-degree opposite X-ray path 520 that connects the focal point of the X-ray source (N_0) 505 with the focal point of the X-ray source (N_180) 510 and the 180-degree opposite X-ray path 525 that connects the focal point of the X-ray source (N+1_0) 515 with the focal point of the X-ray source (N_180) 510.

However, there are not a 180-degree opposite X-ray path that connects a point between the X-ray source (N_0) 505 and the X-ray source (N+1_0) 515 with the focal point of the X-ray source (N_180) 510. Therefore, a part of first-order X-ray data 340 of the interpolation X-ray path 530 is produced using the part of first-order X-ray data 340 corresponding to the 180-degree opposite X-ray path 520 and the part of first-order X-ray data 340 corresponding to the 180-degree opposite X-ray path 525.

As a method of producing the projection data of the interpolation X-ray path 530, there is an example in which linear interpolation is conducted by the following expression (1) with respect to a helical pitch "a+b" to produce the projection data of the interpolation X-ray path 530.

$$\frac{b}{(a+b)}P_N + \frac{a}{(a+b)}P_{N+1} = CP \tag{1}$$

In the expression, $P_N$ denotes the pixel value of the first-order X-ray data 340 of the 180-degree opposite X-ray path 520, $P_{N+1}$ denotes the pixel value of the first-order X-ray data 340 of the 180-degree opposite X-ray path 525, CP denotes the pixel value of the first-order X-ray data 340 of the interpolation X-ray path 530, and "a" and "b" denote a distance between end point of CP and end point of $P_N$ and a distance between end point of CP and end point of $P_{N+1}$, respectively.

As described above, in the case where linear interpolation and extrapolation are conducted to produce the interpolation X-ray path 530, the 180-degree opposite X-ray paths can be present false in all the X-ray irradiation directions, so that the X-ray detection image 330 in the first-order X-ray shield regions can be interpolated using the 180-degree opposite X-ray paths.

In the case where the helical pitch "a+b" is long, there is a case where missing image information caused by the method of interpolating the components in the first-order X-ray shield regions using the surrounding first-order X-ray components is smaller than missing image information caused by the interpolation method using the interpolation X-ray path 530. Accordingly, it is preferable to use a combination of both methods. Even in the case of helical scanning described above in FIG. 5, an effect is provided in that the scattered X-ray data 335 can be extracted and removed to obtain a satisfactory rearrangement image.

Also, within the angle half as large as a maximum cone angle, the interpolation X-ray path 530 can be produced by the method using the above-mentioned expression (1). Therefore, an effect is provided in that projection data at 360-degree directions on a plane forming the angle below half of the maximum cone angle with respect to the rotational axis can be produced to easily rearrange a slice image forming the angle below half of the maximum cone angle with respect to the rotational axis.

Note that, although the method using the expression (1) is the linear interpolation, it is needless to say that the interpolation X-ray path 530 can be obtained by nonlinear interpolation using a function of an actual X-ray path near the interpolation X-ray path 530 to be obtained.

Figure 6:
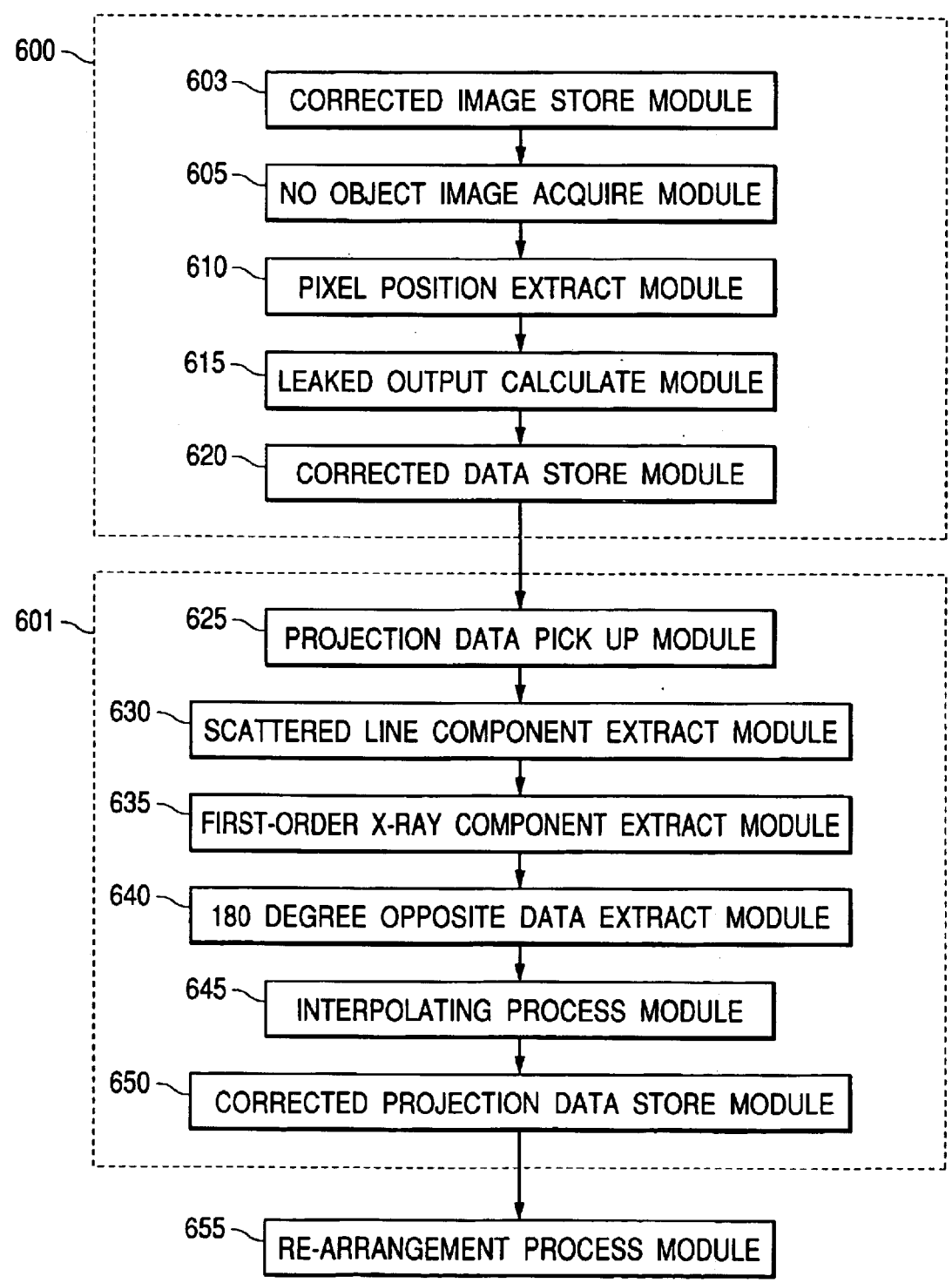
FIG. 6 is an explanatory diagram of a process in a rearrangement process unit shown in FIG. 1.

FIG. 6 is an explanatory diagram of a process in the rearrangement process unit shown in FIG. 1. The process is broadly divided into a preprocess 600 and a main process 601. First, the preprocess 600 will be described.

Reference numeral 603 denotes a corrected image store module that acquires a corrected image for correcting a difference of sensitivities among respective pixels, in which first-order X-ray shields are not held. Reference numeral 605 denotes a no-object image acquire module that acquires an image which does not include a scattered line component by image taking with a state in which the X-ray shields 210 are held and no object is located. Reference numeral 610 denotes a pixel position extract module of the first-order X-ray shield regions that extracts pixel areas of the first-order X-ray shield regions and positions thereof from the image which has no object and is acquired in the no-object image acquire module 605.

Reference numeral 615 denotes a leaked output calculate module that calculates the amount of signal leaked to the first-order X-ray shield regions due to a deterioration of resolution caused by a scintillator and the like. Reference numeral 620 denotes a corrected data store module that stores corrected data for correcting, for example, the difference of sensitivities among the respective pixels, the pixel areas corresponding to the first-order X-ray shield regions, the position information of the first-order X-ray shield regions, and signal leak information of the signal leaked to the first-order X-ray shield regions due to the deterioration of resolution.

An actual process flow of the preprocess 600 will be described. In the corrected image store module 603 in which the first-order X-ray shields are not held, in order to remove the difference of sensitivities among the respective pixels and to remove the unevenness of sensitivities caused by a grid if the grid is attached to the X-ray detection device 115, a gain-corrected image is acquired.

Next, in the no-object image acquire module 605, the first-order X-ray shields are held and an image in the case where no object is located (there is no scattered line) is acquired. In the pixel position extract module 610 of the first-order X-ray shield regions, the pixel areas and the pixel position in the first-order X-ray shield regions are extracted based on the acquired image.

Using the no-object image, a leak of the signal leaked to the first-order X-ray shield regions due to the deterioration of resolution is calculated from the extracted pixel areas and pixel positions in the leaked output calculate module 615 to the first-order X-ray shield regions. This may be conducted by a method in which the resolution of the X-ray detection device 115 is measured in advance and a leak of a signal may be calculated using a resolution restoring filter (for example, a Wiener filter).

In the corrected data store module 620, the gain-corrected image, information with respect to the pixel areas and pixel positions in the first-order X-ray shield regions, and the amount of signal leaked to the first-order X-ray shield regions, which are obtained above, are stored. Given above is the preprocess 600. This process may be conducted before the shipment of products. Alternatively, the process may be conducted at the time of daily maintenance.

Next, the main process 601 will be described. Reference numeral 625 denotes a projection data pick up module that picks up projection data for acquiring a projection data of the actual object. Reference numeral 630 denotes a scattered line component extract module that extracts a scattered X-ray component in X-ray detection image 330, and calculate scattered X-ray data 335. Reference numeral 635 denotes a first-order X-ray component extract module that extracts a first-order X-ray component from X-ray detection image 330, and calculate first-order X-ray data 340.

Reference numeral 640 denotes a 180-degree opposite data extract module that extracts 180-degree opposite data in the first-order X-ray shield regions. Reference numeral 645 denotes an interpolating process module of the first-order X-ray shield regions, which interpolates components in the first-order X-ray shield regions using the extracted 180-degree opposite data. Reference numeral 650 denotes a corrected projection data store module that stores complement image data in which the components in the first-order X-ray shield regions are interpolated.

An actual process flow of the main process 601 will be described. In the projection data pick up module 625 of the object, single scanning or helical scanning is conducted on the object and its vicinities to thereby pick up the projection data of the object at each angle. In the case of picking up, a gain of each pixel of each projection data is corrected using the gain-corrected image.

Next, the scattered line component in each picked up projection data is extracted and scattered X-ray data 335 is calculated by the method as shown in FIG. 3 in the scattered line component extract module 630. A range and position of the first-order X-ray shield region in which only the scattered line component is detected are determined according to the corrected data stored in the preprocess 600. In the case where the scattered line component is extracted, a leak of a signal is calculated from the corrected data stored in the preprocess 600 and the scattered X-ray data 335 is calculated.

In the first-order X-ray component extract module 635, the calculated scattered X-ray data 335 is subtracted from X-ray detection image 330 to obtain the first-order X-ray data 340. In this case, processing for preventing the leak of the signal due to the deterioration of resolution is conducted. Here, the first-order X-ray data 340 corresponding to all of the acquired projection data are calculated, and the group of thus obtained first-order X-ray data are stored. In the 180-degree opposite data extract module 640, 180-degree opposite data corresponding to the first-order X-ray shield region in the calculated first-order X-ray data 340 is extracted from the another first-order X-ray data 340.

In the interpolating process module 645 of the first-order X-ray shield regions, the components in the first-order X-ray shield regions are interpolated using the extracted 180-degree opposite data. If necessary, linear interpolation is conducted using adjacent pixels in the first-order X-ray non-shield regions. Predetermined filtering processing may be conducted or may not be conducted before the interpolation.

Thus, all the projection data are corrected to obtain the first-order X-ray data 340, interpolation is conducted on regions in which no first-order X-ray is radiated, and the corrected complement image data is stored in the corrected projection data store module 650. At this time, for use in the rearrangement process, the pixel area and position information in the first-order X-ray shield region on which the interpolation is conducted are stored in relation to the respective corrected complement image data.

The processes up to this step correspond to the preprocess 600 and the main process 601. After that, a slice image of the object and a three-dimensional image thereof are rearranged using the corrected complement image data in a rearrangement process module 655.

Figure 7:
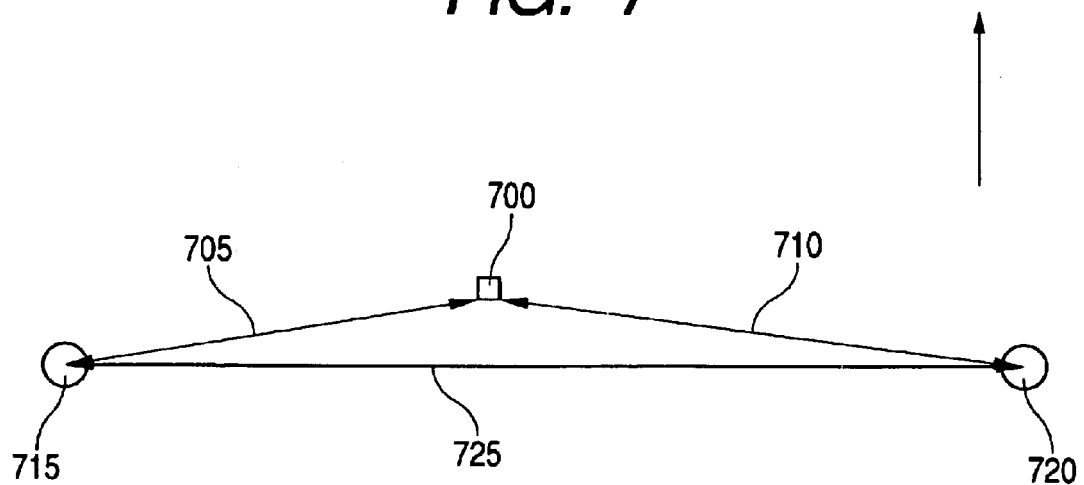
FIG. 7 is an explanatory view of a 180-degree opposite X-ray path selecting method as shown in FIG. 4 in the case where X-rays form a cone beam and single scanning is conducted using a two-dimensional X-ray detection device.

FIG. 7 is an explanatory view of a 180-degree opposite X-ray path selecting method as shown in FIG. 4 in the case where X-rays form a cone beam and single scanning is conducted using the two-dimensional X-ray detection device 115.

Reference numeral 700 denotes a voxel of interest, 705 denotes an X-ray path A, 710 denotes an X-ray path B, 715 denotes an X-ray source A, 720 denotes an X-ray source B, and 725 denotes a rotational plane. Here, the X-ray path A 705 is an X-ray path which extends from the focal point of the X-ray source A 715 and passes through the voxel of interest 700. The X-ray path B 710 is an X-ray path which extends from the focal point of the X-ray source B 720 and passes through the voxel of interest 700.

In the case where X-rays form a cone beam and single scanning is conducted using the two-dimensional X-ray detection device 115, a rearrangement image can be obtained in the rotational axis direction (which is indicated by an arrow in the drawing). In the case where the rotational plane shown in FIG. 4 is viewed from the direction perpendicular to the rotational axis, the rotational plane corresponds to the rotational plane 725. In addition, the X-ray source 400 corresponds to the X-ray source A 715 and the X-ray source 405 corresponds to the X-ray source B 720.

In the case where the voxel of interest 700 is projected onto the rotational plane in the rotational axis direction, it is assumed that a projection point exists on the 180-degree opposite X-ray path 420. At this time, there is a method of conducting interpolation on the X-ray shield regions by applying the X-ray path A 705 and the X-ray path B 710 to the 180-degree opposite X-ray path 420 shown in FIG. 4.

Thus, as compared with the case where the one-dimensional X-ray detection device 115 is used, in the case where two-dimensional X-ray detection device 115 is used, an effect is provided in that an image taking time is short because a large number of cross-sections of the object can be obtained by single scanning.

The above description relates to the case of the single scanning and the example in which the focal point of the X-ray source 100 is rotated within the same plane. In contact to this, in the case where the X-ray source 100 is helically moved about a rotational axis 118 as shown in FIG. 5, the focal point of the X-ray source 100 is not rotated within the same plane. In either case, with respect to the voxel of interest 700, a pair of X-ray paths in which an angle formed by the X-ray path B 710 and the X-ray path A 715 becomes maximum are selected as a pair of 180-degree opposite X-ray paths. Therefore, even in the case the X-ray source 100 is helically moved, interpolation processing can be conducted on the first-order X-ray image 340. In the example described with reference to FIG. 5, the 180-degree opposite X-ray paths are interpolated using the two X-ray paths, which do not pass through the voxel of interest 700. For example, in the case where a substance having strong X-ray absorption is present in the position of the voxel of interest, if the 180-degree opposite X-ray paths are determined by the method described here, the rearrangement processing can be conducted with higher precision.

Figure 8:
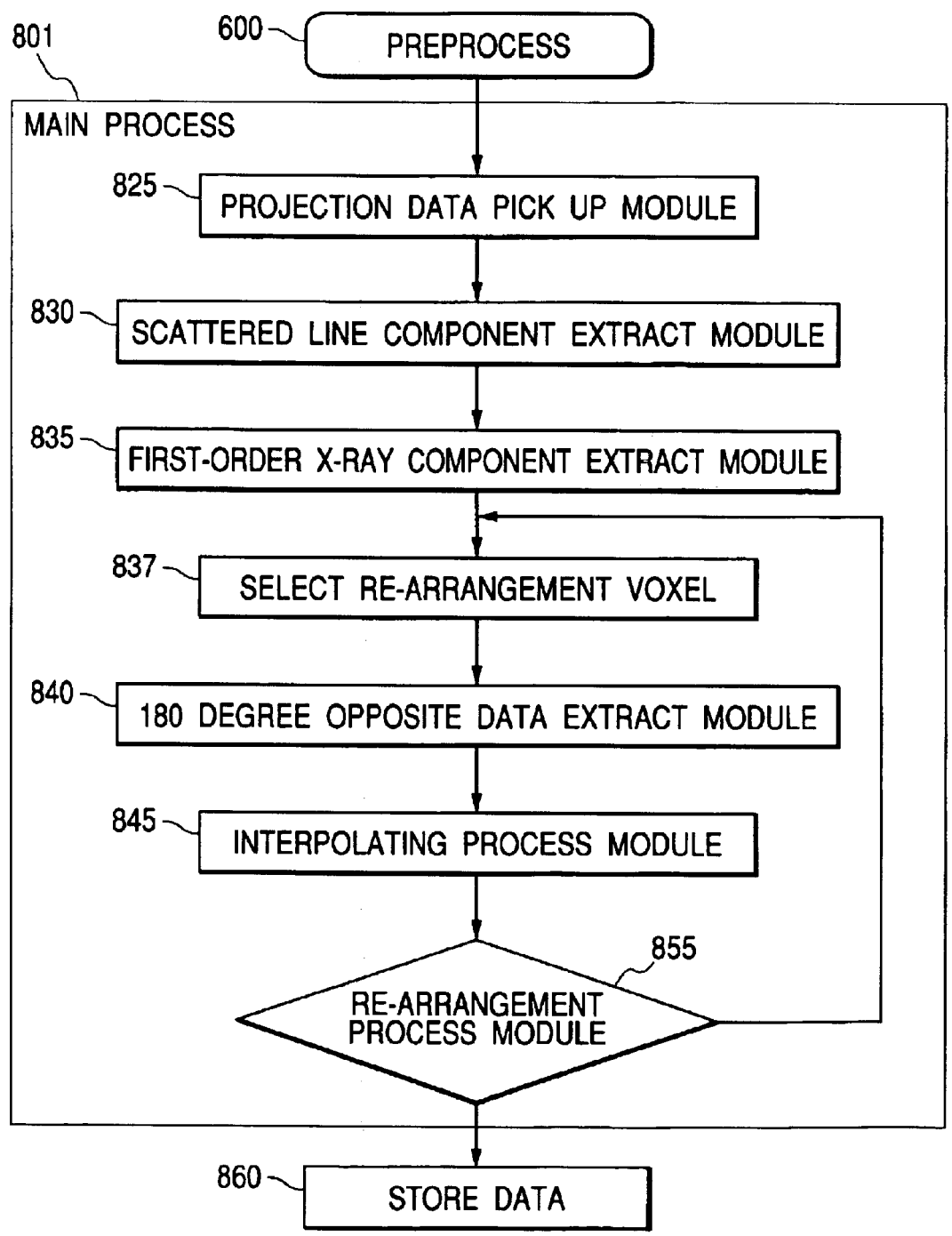
FIG. 8 is an explanatory view of a process executed in rearrangement process unit in FIG. 1 in the case where a pair of 180-degree opposite X-ray paths passes on remarked voxel.

In FIG. 8, reference numerals 801, 825, 830, 835, 837, 840, 845, 855, and 860 denote processes in the main process 601 described with reference to FIG. 6 in the case where a pair of 180-degree opposite X-ray paths pass through the voxel of interest. A preprocess is the same as the preprocess 600 shown in FIG. 6. Hereinafter, a main process 801 will be described. Reference numeral 825 denotes a projection data pick up module that picks up projection data of the object. Reference numeral 830 denotes a scattered line component extract module that extracts a scattered line component from the X-ray detection image 330 to obtain the scattered X-ray data 335. Reference numeral 835 denotes a first-order X-ray data extract module that extracts a first-order X-ray component from the X-ray detection image 330 to obtain the first-order X-ray data 340. Reference numeral 837 denotes a rearrangement voxel selection module that selects voxels to be rearranged. Reference numeral 840 denotes a 180-degree opposite data extract module that extracts 180-degree opposite data in the first-order X-ray shield regions. Reference numeral 845 denotes an interpolating process module that interpolates components in the first-order X-ray shield regions using the extracted 180-degree opposite data. Reference numeral 855 denotes a rearrangement process module that rearranges the selected voxels of interest using an interpolation image in which components in the first-order X-ray shield regions are interpolated. Reference numeral 860 denotes a data store module that stores the rearranged voxel data.

An actual process flow of the main process 801 will be described. In the projection data pick up module 825 that picks up the projection data of the object, single scanning or helical scanning is conducted about the object to pick up the projection data of the object at each angle. In the case of picking up, a gain of each pixel of each projection data is corrected using the gain-corrected image. Next, in the scattered X-ray image extract module 830, the scattered X-ray image in each picked up projection data is extracted by the method as shown in FIG. 3 to obtain the scattered X-ray data 335. Here, a range and a position of the first-order X-ray shield region in which only the scattered X-ray image is detected are determined according to the corrected data stored in the preprocess 600. In the case where the scattered X-ray image is extracted, a leakage of a signal is calculated from the corrected data stored in the preprocess 600 to obtain the scattered X-ray data 335. In the first-order X-ray component extract module 835, the obtained scattered line image 335 is subtracted from the X-ray detection image 330 to obtain the first-order X-ray data 340. Also, in this case, processing for preventing the leakage of the signal due to the deterioration of solution is conducted. Here, the first-order X-ray data 340 corresponding to all the obtained projection data is obtained and the first-order X-ray data group is stored. In the rearrangement voxel selection module 837, voxels to be rearranged in a three dimensional space are selected. In the 180-degree opposite data extract module 840, data of the 180-degree opposite X-ray paths corresponding to the first-order X-ray shield region in the obtained first-order X-ray data 340 is extracted from another first-order X-ray data 340. At this time, each data of the 180-degree opposite X-ray paths is extracted such that the pair of 180-degree opposite X-ray paths pass through the voxel of interest. In the interpolating process module 845 of the first-order X-ray shield regions, the components in the first-order X-ray shield regions are interpolated using the extracted 180-degree opposite data. The rearrangement process module 855 rearranges the voxels of interest in only the first-order X-ray shield regions required for rearranging the voxels of interest, using the interpolation image obtained by partial interpolation. In the rearrangement process module 855, the processes conducted by the modules from the rearrangement voxel selection module 837 to the rearrangement process module 855 has been repeated until the rearrangment processing has been conducted on all voxels to be rearranged. After the rearrangment processing is conducted on all voxels to be rearranged, the processed voxel group is stored in the data store module 860.

As described above, with respect to a slice image of the object and a three-dimensional image thereof, the scattered line resulting from the object causes the deterioration of the image quality of the rearrangement image. According to the X-ray computed tomography apparatus of the present invention, an effect is provided in that the scattered line component resulting from the object can be removed from the projection data to thereby obtain a satisfactory rearrangement image.

Note that the present invention may be applied to either a system constituted by a plurality of apparatuses (e.g., image processing apparatuses, interfaces, radiographic apparatuses, X-ray generation apparatuses, and the like) or an arrangement that integrates an image processing apparatus and a radiographic apparatus, or the like.

The present invention is not limited to the above embodiment and various-changes and modifications can be made within the spirit and scope of the present invention. Therefore to apprise the public of the scope of the present invention, the following claims are made.

What is claimed is:

1. An X-ray computed tomography apparatus, comprising:
   an X-ray source that radiates an X-ray to an object;
   an X-ray detection device that converts the X-ray passing through the object into X-ray detection image data;
   at least one X-ray shield located between a focal point of the X-ray source and the X-ray detection device;
   control means for performing control so as to relatively move the X-ray source and the object;
   scattered line removing means for calculating a scattered X-ray data component corresponding to a scattered X-ray component from X-ray detection image data corresponding to a region in which a first-order X-ray is shielded by the X-ray shield and calculating a first-order X-ray image data obtained by removing the scattered X-ray component from the X-ray detection image data;
   complementing means for calculating complemented image data from the first-order X-ray image data by complementing a part of the first-order X-ray image data corresponding to the region in which the first-order X-ray is shielded; and
   rearranging means for rearranging an image by reversely projecting the complement image data,
   wherein the complementing means complements the part of the first-order X-ray image data obtained by shielding the first-order X-ray, corresponding to an X-ray path connecting the focal point of the X-ray source with the X-ray shield by using another part of the first-order X-ray image data obtained by the first-order X-ray in non-shield state, corresponding to an X-ray path in a 180-degree opposite direction to the X-ray path connecting the focal point of the X-ray source with the X-ray shield.

2. An X-ray computed tomography apparatus according to claim 1, wherein the X-ray shields are asymmetrically arranged with respect to a plane including the focal point of the X-ray source and a rotation axis about which the object and the X-ray source are relatively rotated.

3. An X-ray computed tomography apparatus according to claim 1, wherein the X-ray shield is located between the X-ray source and the object.

4. An X-ray computed tomography apparatus according to claim 1, wherein the X-ray detection device includes pixels arranged in two-dimensional matrix.

5. An X-ray computed tomography apparatus according to claim 1, wherein the relative movement between the X-ray source and the object is a helical movement.

6. An X-ray computed tomography apparatus, comprising:
   an X-ray source that radiates an X-ray to an object;
   an X-ray detection device that converts the X-ray passing through the object into X-ray detection image data;
   at least one X-ray shield located between a focal point of the X-ray source and the X-ray detection device;
   control means for performing control so as to relatively move the X-ray source and the object;
   scattered line removing means for calculating a scattered X-ray data component corresponding to a scattered X-ray component from X-ray detection image data corresponding to a region in which a first-order X-ray is shielded by the X-ray shield and calculating a first-order X-ray image data obtained by removing the scattered X-ray component from the X-ray detection image data;
   complementing means for calculating complemented image data from the first-order X-ray image data by complementing a part of the first-order X-ray image data corresponding to the region in which the first-order X-ray is shielded; and
   rearranging means for rearranging an image by reversely projecting the complement image data,
   wherein the complementing means complements the part of the first-order X-ray image data obtained by shielding the first-order X-ray, corresponding to an X-ray path connecting the focal point of the X-ray source with the X-ray shield by using another part of the first-order X-ray image data obtained by converting an X-ray radiated along an X-ray path closest to a path in the 180-degree opposite direction when an X-ray path in the 180-degree opposite direction does not exist.

* * * * *